United States Patent
Lykotrafitis et al.

(10) Patent No.: US 10,928,289 B2
(45) Date of Patent: Feb. 23, 2021

(54) ASSEMBLY FOR MEASURING THE VISCOSITY OF FLUIDS USING MICROCHANNELS

(71) Applicant: University of Connecticut, Farmington, CT (US)

(72) Inventors: George Lykotrafitis, South Windsor, CT (US); Kostyantyn Partola, Manchester, CT (US)

(73) Assignee: University of Connecticut, Farmington, CT (US)

( * ) Notice: Subject to any disclaimer, the term of this patent is extended or adjusted under 35 U.S.C. 154(b) by 92 days.

(21) Appl. No.: 15/970,226

(22) Filed: May 3, 2018

(65) Prior Publication Data

US 2018/0321124 A1    Nov. 8, 2018

Related U.S. Application Data

(60) Provisional application No. 62/501,415, filed on May 4, 2017.

(51) Int. Cl.
*G01N 11/08* (2006.01)
*G01N 33/49* (2006.01)
(Continued)

(52) U.S. Cl.
CPC .............. *G01N 11/08* (2013.01); *G01N 11/06* (2013.01); *G01N 33/49* (2013.01); *G01N 2011/008* (2013.01); *G01N 2011/0026* (2013.01)

(58) Field of Classification Search
CPC ...... G01F 1/7086; G01N 11/06; G01N 11/04; G01N 2011/0026
See application file for complete search history.

(56) References Cited

U.S. PATENT DOCUMENTS 4,554,821 A * 11/1985 Kiesewetter ........... G01N 11/06
                                                           73/54.07
5,099,698 A     3/1992 Kath et al.
(Continued)

OTHER PUBLICATIONS

Yoon et al., "Generation of digitized microfluidic filling flow by vent control", Biosensors and Bioelectronics, No. 92, Oct. 28, 2016. (Year: 2016).*

(Continued)

*Primary Examiner* — David A. Rogers
(74) *Attorney, Agent, or Firm* — McCarter & English, LLP (57) ABSTRACT

The present disclosure provides improved viscosity measuring assemblies, and related methods of use. More particularly, the present disclosure provides advantageous measuring assemblies configured to measure the viscosity of samples/fluids (e.g., opaque or transparent liquids) using microchannels. The present disclosure provides for a viscosity measuring assembly (e.g., hand-held electronic measuring assembly) that is configured to measure the viscosity of samples/fluids (e.g., opaque or transparent Newtonian and non-Newtonian liquids, including blood, etc.), in a short period of time (e.g., within a couple of minutes) utilizing only about a droplet of fluid. The viscosity measuring assembly can include a substrate having a microchannel, a light source (e.g., a collimated low coherence light source), and a sensor (e.g., photodiode). The micro-channeled substrate may be disposable, and some of the other components may be reusable since they are substantially not directly exposed to the sample during operation of the viscosity measuring assembly.

22 Claims, 6 Drawing Sheets

(51) Int. Cl.
*G01N 11/06* (2006.01)
*G01N 11/00* (2006.01)

(56) References Cited

U.S. PATENT DOCUMENTS

| | | | | |
|---|---|---|---|---|
| 5,410,145 | A * | 4/1995 | Coroy | G01J 1/44 250/214 C |
| 5,843,691 | A * | 12/1998 | Douglas | C12Q 1/54 435/14 |
| 6,322,524 | B1 * | 11/2001 | Kensey | A61B 5/02035 600/573 |
| 6,402,703 | B1 * | 6/2002 | Kensey | A61B 5/02035 600/573 |
| 6,428,488 | B1 * | 8/2002 | Kensey | A61B 5/02035 600/573 |
| 6,669,831 | B2 * | 12/2003 | Chow | B01J 19/0093 137/804 |
| 6,745,615 | B2 * | 6/2004 | Kensey | A61B 5/02035 73/54.04 |
| 6,907,772 | B2 * | 6/2005 | Kensey | A61B 5/02035 73/54.04 |
| 7,022,286 | B2 * | 4/2006 | Lemke | B01L 3/5027 422/67 |
| 7,188,515 | B2 * | 3/2007 | Burns | B82Y 15/00 702/50 |
| 7,770,436 | B2 * | 8/2010 | Baek | G01N 11/08 73/54.09 |
| 8,475,734 | B2 * | 7/2013 | Neijzen | B01L 3/502753 422/408 |
| 10,386,282 | B2 * | 8/2019 | Colomer Farrarons | G01N 11/04 |
| 10,502,754 | B2 * | 12/2019 | Chung | G01F 1/661 |
| 2002/0046948 | A1 * | 4/2002 | Chow | B01J 19/0093 204/450 |
| 2002/0088953 | A1 * | 7/2002 | Kensey | A61B 5/02035 250/577 |
| 2003/0210287 | A1 * | 11/2003 | Harding | B01L 3/5027 347/1 |
| 2006/0179923 | A1 * | 8/2006 | Burns | B82Y 15/00 73/54.07 |
| 2008/0134765 | A1 * | 6/2008 | Baek | G01N 11/08 73/54.09 |
| 2009/0240123 | A1 * | 9/2009 | Siebrecht | A61B 5/02028 600/310 |
| 2009/0282901 | A1 * | 11/2009 | Leonard | G01N 11/06 73/54.02 |
| 2010/0005866 | A1 * | 1/2010 | Sebok | G01F 1/7086 73/54.43 |
| 2010/0191482 | A1 * | 7/2010 | Hasson | G01F 1/7086 702/49 |
| 2014/0106382 | A1 * | 4/2014 | Williamson | G01N 33/49 435/13 |
| 2016/0025535 | A1 * | 1/2016 | Byers | G01F 1/7086 73/861.08 |
| 2016/0305864 | A1 | 10/2016 | Vanapalli et al. | |
| 2016/0339433 | A1 * | 11/2016 | Hasson | C12Q 1/686 |
| 2018/0321124 | A1 * | 11/2018 | Lykotrafitis | G01N 11/08 |

OTHER PUBLICATIONS

Bianco et al., "Integrated microfluidic viscometer for edible oil analysis", Sensors and Actuators, Mar. 7, 2018. (Year: 2018).*
Elizalde et al., "Precise capillary flow for paper-based viscometry", Microfluid Nanofluid, Sep. 14, 2016. (Year: 2016).*
Srivastava et al., "Nanoliter Viscometer for Analyzing Blood Plasma and Other Liquid Samples", Analytical Chemistry, No. 77, Dec. 7, 2004. (Year: 2004).*
Excelitas Photodiodes Application Notes, archived Mar. 4, 2016 and available on the internet at <http://web.archive.org/web/20160304182654/http://www.pacer.co.uk/assets/pacer/user/photodiodes.pdf> (Year: 2016).*
Srivastava, et al., Nanoliter Viscometer for Analyzing Blood Plasma and Other Liquid Samples, Analytical Chemistry, vol. 77, No. 2, pp. 383-392, published Jan. 15, 2005.
Srivastava, et al., Analysis of Non-Newtonian Liquids Using a Microfluidic Capillary Viscometer, Analytical Chemistry, vol. 78, No. 5, pp. 1690-1696, published Mar. 1, 2006.
Quist, et al., Piezoresistive Cantilever Based on Nanoflow and Viscosity Sensor for Microchannels, Lab on a Chip, 6, pp. 1450-1454, published on web Sep. 1, 2006.
Nguyen et al., Micofluidic Rheometer Based on Hydrodynamic Focusing, Measurement Science and Technology, 19, pp. 1-9, published Jun. 30, 2008.
Chevalier, et al., Microfluidic on Chip Viscometers, Review of Scientific Instruments, 79, pp. 1-3, published on web Jul. 2, 2008.
Graham-Rowe, A Portable, Cheap Blood-Clotting Test, MIT Technology Review, published Nov. 10, 2008.
Kang, et al., A Highly Accurate and Consistent Microfluidic Viscometer for Continuous Blood Viscosity Measurement, Artifical Organs, vol. 34, No. 11, pp. 944-949, published on Nov. 11, 2010.
Kang, et al., Integrated Microfluidic Viscometer Equipped with Fluid Temperature Controller for Measurement of Viscosity in Complex Fluids, Microfluid Nanofluid, 14, pp. 657-668, published 2013.
Kang, et al., Label-free Viscosity Measurement of Complex Fluids Using Reversal Flow Switching Manipulation in a Microfluidic Channel, Biomicrofluidics, 7, 044106, pp. 1-16, published on web Jul. 26, 2013.
Morhell, et al., Power Law Fluid Viscometry Through Capillary Filling in a Closed Microchannel, Sensors and Actuators B: Chemical, 227, pp. 24-28, published on web Dec. 13, 2015.
Yoon, et al., Generation of Digitized Microfluidic Filling Flow by Vent Control, Biosensors and Bioelectronics, 92, pp. 465-471, published on web Oct. 28, 2016.
U.S. Appl. No. 62/501,415, filed May 4, 2017.

* cited by examiner

ASSEMBLY FOR MEASURING THE VISCOSITY OF FLUIDS USING MICROCHANNELS

CROSS-REFERENCE TO RELATED APPLICATION

The present application claims priority benefit to a provisional application entitled "Assembly for Measuring the Viscosity of Fluids Using Microchannels," which was filed on May 4, 2017, and assigned Ser. No. 62/501,415. The entire content of the foregoing provisional patent application is incorporated herein by reference.

FIELD OF THE DISCLOSURE

The present disclosure relates generally to the field of viscosity measuring assemblies and, more particularly, to measuring assemblies configured to measure the viscosity of samples/fluids (e.g., opaque or transparent liquids) using microchannels.

BACKGROUND OF THE DISCLOSURE

In general, commercially available rheometers (e.g., viscometers for non-Newtonian fluids) require large sums of the sample, take a long time to gather measurements (e.g., hours) and can be expensive (e.g., $5000 or more) because they can be configured to meet a large variety of typically industrial applications. The parts of the device that typically come in contact with the sample can require maintenance and can be expensive to replace (e.g., $200 or more). As such, these rheometers are generally not currently used in health care.

Alternative solutions have been proposed, such as some microchannel or capillary based devices, however, in most cases these devices still require a long time to conduct the measurement due to manual signal processing, such as direct video processing, and are often as expensive as their counterparts. Moreover, these devices can be expensive in time and money to fully manufacture, and may not be reasonably extended to a full consumer product.

An interest exists for improved viscosity measuring assemblies and related methods of use. These and other inefficiencies and opportunities for improvement are addressed and/or overcome by the assemblies, systems and methods of the present disclosure.

SUMMARY OF THE DISCLOSURE

The present disclosure provides improved viscosity measuring assemblies, and related methods of use. More particularly, the present disclosure provides advantageous measuring assemblies configured to measure the viscosity of samples/fluids (e.g., opaque or transparent liquids) using microchannels.

In exemplary embodiments, the present disclosure provides for a hand-held electronic measuring assembly which is configured and adapted to measure the viscosity of fluids (e.g., opaque or transparent Newtonian and non-Newtonian liquids, including blood), within a couple of minutes utilizing substantially only about a droplet of fluid/liquid.

Some important components of the measuring assembly to allow for the measurements are a substrate having a microchannel, a light source (e.g., a collimated low coherence light source), and a sensor/detector (e.g., photodiode). In exemplary embodiments, the micro-channeled substrate is disposable. Some of the other components may be reusable since they are substantially not directly exposed to the sample during standard operation.

In exemplary embodiments, the measuring assembly can be used to measure the viscosity of blood (a non-Newtonian fluid), which has been found to correlate directly with cardiovascular events, such as ischemic heart disease and stroke. As such, medical labs and practitioners can utilize the advantageous measuring assembly of the present disclosure to quickly and economically measure their patients' blood viscosity and evaluate the patients' risk for such disorders. It is noted that the measuring assembly may also be useful in other fields (e.g., for evaluating the viscosity of substances/fluids such as engine oil, paint or printing inks, etc.).

The present disclosure provides for a measuring assembly including a substrate having a microchannel extending from a first end to a second end; a light source positioned over a top surface of the substrate; a sensor positioned under a bottom surface of the substrate; wherein after a fluid sample is introduced to the first end of the microchannel, light from the light source is detected by the sensor through regions of the microchannel not containing the fluid sample to produce signals that are utilized to record how far along the microchannel the fluid sample has progressed after several time periods to determine the viscosity of the fluid sample.

The present disclosure also provides for a measuring assembly wherein the fluid sample is an opaque or transparent liquid. The present disclosure also provides for a measuring assembly wherein the fluid sample is blood.

The present disclosure also provides for a measuring assembly wherein the light source is a collimated low coherence light source. The present disclosure also provides for a measuring assembly wherein the substrate is transparent. The present disclosure also provides for a measuring assembly wherein the sensor is a photodetector. The present disclosure also provides for a measuring assembly wherein the sensor is a reverse-biased photodiode.

The present disclosure also provides for a measuring assembly wherein the light source and the sensor are not directly exposed to the fluid sample during introduction of the fluid sample to the first end of the microchannel. The present disclosure also provides for a measuring assembly wherein the fluid sample is about 500 μL or less.

The present disclosure also provides for a measuring assembly further including a pressor sensor configured and adapted to measure the pressure inside the microchannel.

The present disclosure also provides for a measuring method including providing a substrate having a microchannel extending from a first end to a second end; positioning a light source over a top surface of the substrate; positioning a sensor under a bottom surface of the substrate; introducing a fluid sample to the first end of the microchannel; and detecting light from the light source by the sensor through regions of the microchannel not containing the fluid sample to produce signals that are utilized to record how far along the microchannel the fluid sample has progressed after several time periods to determine the viscosity of the fluid sample.

The present disclosure also provides for a measuring method wherein the fluid sample is an opaque or transparent liquid. The present disclosure also provides for a measuring method wherein the fluid sample is blood. The present disclosure also provides for a measuring method wherein the light source is a collimated low coherence light source.

The present disclosure also provides for a measuring method wherein the substrate is transparent. The present disclosure also provides for a measuring method wherein the sensor is a photodetector. The present disclosure also provides for a measuring method wherein the sensor is a reverse-biased photodiode.

The present disclosure also provides for a measuring method wherein the light source and the sensor are not directly exposed to the fluid sample during introduction of the fluid sample to the first end of the microchannel. The present disclosure also provides for a measuring method wherein the fluid sample is about 500 µL or less.

The present disclosure also provides for a measuring method further including a pressor sensor configured and adapted to measure the pressure inside the microchannel.

Any combination or permutation of embodiments is envisioned. Additional advantageous features, functions and applications of the disclosed assemblies, systems and methods of the present disclosure will be apparent from the description which follows, particularly when read in conjunction with the appended figures. All references listed in this disclosure are hereby incorporated by reference in their entireties.

BRIEF DESCRIPTION OF THE DRAWINGS

Features and aspects of embodiments are described below with reference to the accompanying drawings, in which elements are not necessarily depicted to scale.

Exemplary embodiments of the present disclosure are further described with reference to the appended figures. It is to be noted that the various features, steps and combinations of features/steps described below and illustrated in the figures can be arranged and organized differently to result in embodiments which are still within the scope of the present disclosure. To assist those of ordinary skill in the art in making and using the disclosed assemblies, systems and methods, reference is made to the appended figures, wherein:

FIG. 2 is a partial side view of an exemplary measuring assembly.

FIGS. 4A-4C display the results of exemplary validation experiments; FIG. 4A shows the photodiode signal corresponding with the fluid/liquid column length is linear and repeatable; minor variations occurred at each point due to the visual estimation of the fluid/liquid column length (p<0.05 for the linear fit); FIG. 4C shows the measured viscosity of red blood cells suspended in Alsever's solution; and FIG. 5 is a flowchart depicting three modes of operation for an exemplary viscosity measuring assembly according to the present disclosure; as shown in FIG. 5, a viscosity measuring assembly can be constructed and/or operated in at least three different configurations.

DETAILED DESCRIPTION OF DISCLOSURE

The exemplary embodiments disclosed herein are illustrative of advantageous measuring assemblies, and systems of the present disclosure and methods/techniques thereof. It should be understood, however, that the disclosed embodiments are merely exemplary of the present disclosure, which may be embodied in various forms. Therefore, details disclosed herein with reference to exemplary measuring assemblies/fabrication methods and associated processes/techniques of assembly and use are not to be interpreted as limiting, but merely as the basis for teaching one skilled in the art how to make and use the advantageous viscosity measuring assemblies/systems and/or alternative assemblies of the present disclosure.

The present disclosure provides improved viscosity measuring assemblies, and related methods of use. More particularly, the present disclosure provides improved measuring assemblies configured to measure the viscosity of samples/fluids (e.g., opaque or transparent liquids) using microchannels.

In some embodiments, the present disclosure provides for a viscosity measuring assembly (e.g., hand-held electronic measuring assembly) that is configured to measure the viscosity of samples/fluids (e.g., blood, other liquids, etc.), in a short period of time (e.g., within a couple of minutes) utilizing only about a droplet of fluid/liquid.

In exemplary embodiments, the viscosity measuring assembly includes a substrate having a microchannel, a light source (e.g., a collimated low coherence light source), and a sensor/detector component (e.g., photodiode). The micro-channeled substrate may be disposable, and some of the other components may be reusable since they are substantially not directly exposed to the sample during operation of the viscosity measuring assembly.

An exemplary measuring assembly can be used to measure the viscosity of blood (a non-Newtonian fluid), which can correlate directly with cardiovascular events (e.g., ischemic heart disease, stroke, etc.). As such, medical personnel can advantageously utilize the measuring assembly to quickly and economically measure blood viscosity and evaluate the patients' risk for such disorders. The measuring assemblies of the present disclosure may also be useful in other fields (e.g., for evaluating the viscosity of substances/fluids such as engine oil, paints, printing inks, petroleum, nanoparticle solutions, food additives, personal care products, coatings, adhesives, etc.).

A number of studies have found correlations between whole blood viscosity and cardiovascular disorders, including a 1996 study that followed over 1,500 patients (Sloop 1996; Lowe, Lee et al. 1997; Ciuffetti, Schillaci et al. 2005; Jeong, Cho et al. 2010). This quantity (whole blood viscosity) is generally not currently measured in patients due to many factors (e.g., the cost in time, money, and/or sample size of using a traditional rheometer).

The measuring assembly of the present disclosure is much faster (e.g., requiring only about three minutes instead of hours), uses much less fluid/liquid (e.g., about 500 µL or less is sufficient), is much more affordable (final price will be thousands of dollars cheaper), and is much simpler to fabricate/manufacture.

In exemplary embodiments, the substrate (e.g., transparent micro-channeled substrate) of the measuring assembly (e.g., the substantially only portion of the assembly that is in contact with the sample fluid/liquid) is easy to manufacture, cheap, and disposable, making it particularly suitable for biological samples, unlike commercially available rheometers. Since the micro-channeled substrate is disposable, the sensor/detector component does not need to be sterilized during standard operation. Moreover, the exemplary measuring assembly generally will not require manual data processing.

A microchannel is a channel in which at least one dimension of the cross-section is less than 1 millimeter. Typically, a microchannel cross-section is either rectangular or circular, but it is not limited to these shapes. At this scale, fluid flow is often dominated by capillary and viscous forces that are usually negligible at larger scales. (Folch 2016)

In exemplary embodiments, the measuring assembly of the present disclosure uses a unique sensor/detector system to monitor the progress of the fluid (e.g., liquid) through the microchannel of the substrate. A controlled light source above the substrate illuminates the transparent micro-channeled substrate, and the light from this source is captured by a photodiode on the other side of the micro-channeled substrate. As the opaque fluid traverses the microchannel, it casts a shadow onto the photodiode. The intensity of the light that hits the photodiode produces a corresponding current that can be used to gauge how far along the microchannel the fluid has progressed. In the case of a transparent sample liquid, a method based on differential interference contrast microscopy (DICM) or on dark-field microscopy can be developed in further studies and can be used to create contrast between the sample transparent liquid and the air that initially fills the microchannel.

Since one knows the dimensions of the microchannel, one can measure the capillary pressure directly inside the microchannel itself by sealing (e.g., via a valve or the like) the far end of the microchannel (opposite the fluid entry) and measuring the equilibrium point of the fluid using this sensor, or by directly measuring the pressure via a pressure sensor. Upon release of this valve, the fluid traverses the microchannel and the velocities at which it does this combined with the known pressure can be used to measure the viscosity of the fluid.

For many non-Newtonian liquids (e.g., blood), temperature is crucial to the viscosity of the liquid. Variations in temperature can cause significant changes in the liquid viscosity. For this purpose, heating elements may be utilized to control the temperature of the liquid during the viscosity measurement. For example, a heating element may be placed in close proximity to the substrate as a reusable component or may be associated with the disposable substrate. In the first instance, where the heater is reusable and is placed in close proximity to the substrate, the substrate must reach thermal equilibrium with the heating element(s) before the liquid sample is introduced to it. In a second instance, where the heating element(s) is/are associated with the substrate, the substrate will require an electrical interface to ensure the reusable components are capable of powering the heating element(s). In such case, the substrate may require a period of time to reach the appropriate temperature.

Alternatively, a pressure sensor can be used to directly measure the capillary pressure during the viscosity measurement.

It is noted that many commercially available technologies (e.g., rheometers) are based on mechanically deforming the sample and measuring the sample response versus the rate of deformation. The implemented sensors are electronic gauges that measure deformation. A weak point of conventional technologies based on microchannels is that the correlation between viscosity and output is not easily quantifiable, but it can require intelligent image processing to produce a meaningful output. In exemplary embodiments, the measuring assembly of the present disclosure utilizes an easy method based on light absorption—the output is directly recorded from the photodiode with minimal signal processing.

It is noted that in further studies, the measuring assembly can be miniaturized.

Moreover, nominal light levels, the electronic circuit, the user interface, as well as a signal processing unit may be selected and/or developed.

It is also noted that one can utilize other samples/fluids (other than blood) for calibration of the measuring assembly. As such, experiments can be conducted to test the measuring assembly for fluids/liquids other than blood.

The present disclosure will be further described with respect to the following examples; however, the scope of the disclosure is not limited thereby. The following examples illustrate the advantageous measuring assemblies, systems and methods of the present disclosure.

EXAMPLE 1

In exemplary embodiments, the present disclosure provides a new and advantageous viscosity measuring assembly/method, as discussed further below.

Figure 1:
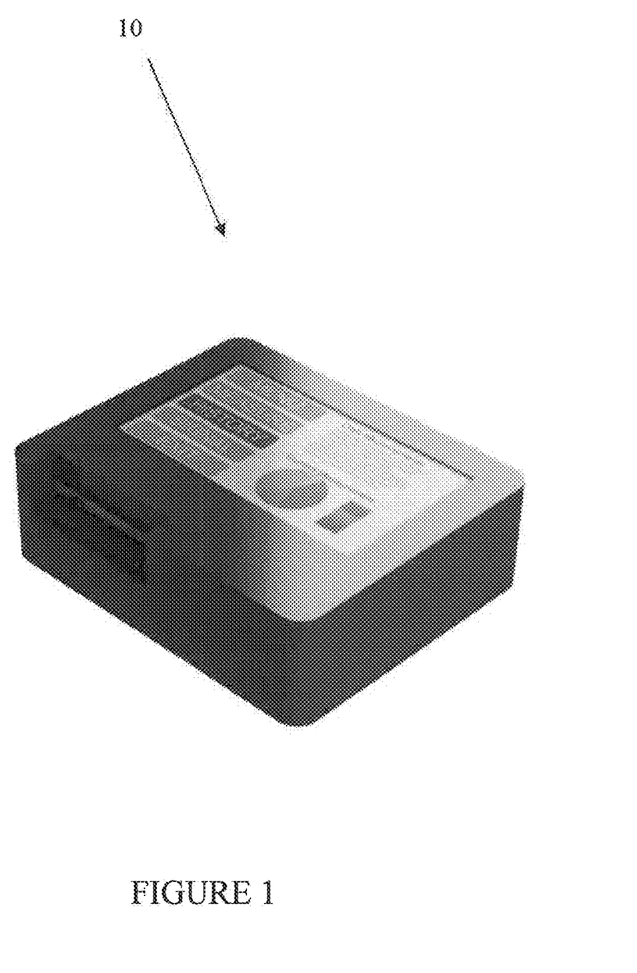
FIG. 1 is a top perspective view of an exemplary viscosity measuring assembly according to the present disclosure.
Figure 2:
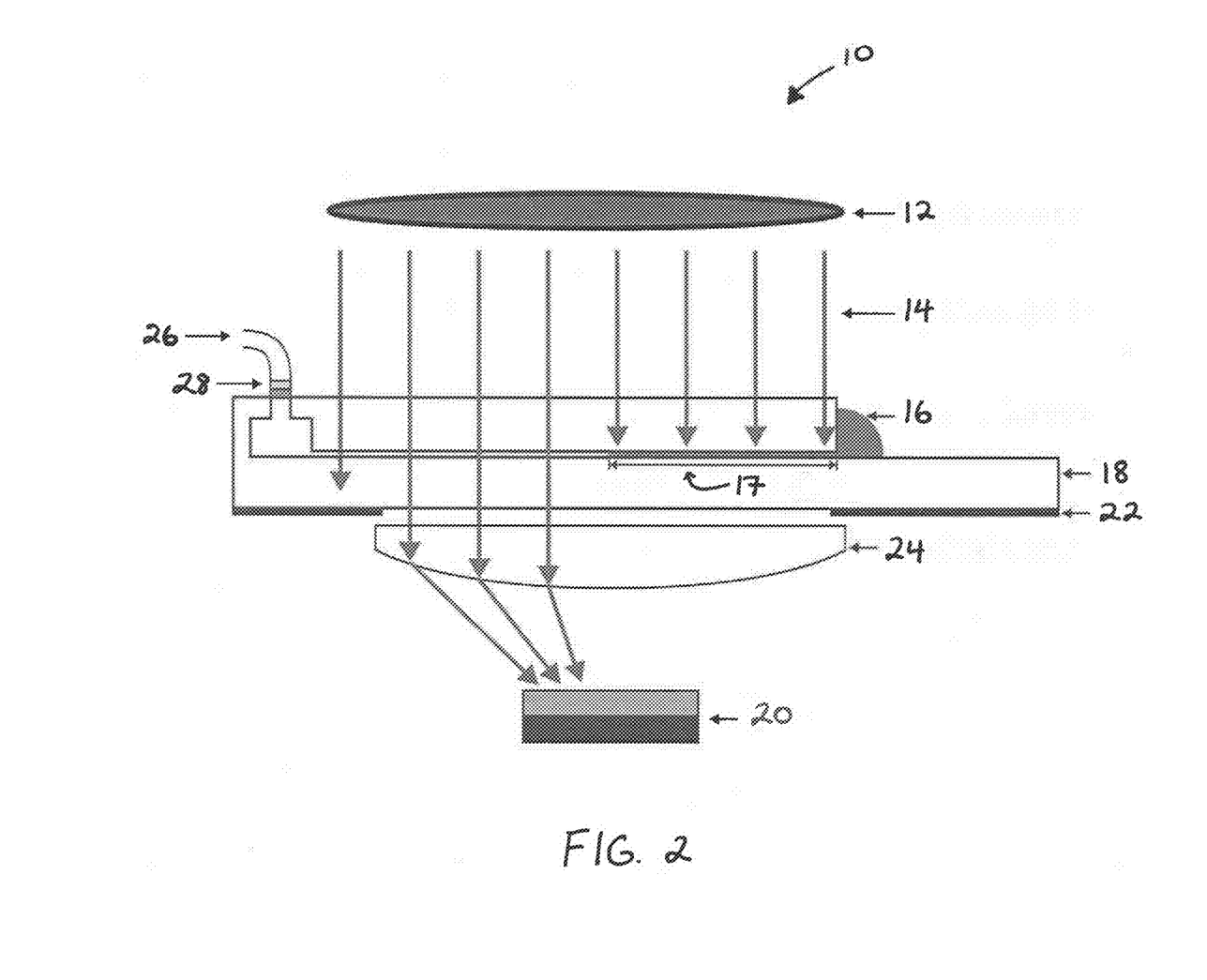
FIG. 2 shows a schematic of the functionality of an exemplary assembly; obstructed light does not fully transmit through the fluid/liquid and only partially reaches the photodiode resulting in lower electrical response compared to unobstructed light; the photodiode electrical response is then proportional to the fluid/liquid progression through the micro-channel.

As shown in FIGS. 1-2, an exemplary measuring assembly 10 of the present disclosure can measure the viscosity of whole blood 16 and of other opaque fluids 16 (e.g., liquids). A small amount of the sample fluid 16 (e.g., about 20 µL) is sufficient, and the sample 16 can be deposited in contact with a microchannel opening of the substrate 18 (FIG. 2).

At the other end (e.g., opposite the fluid 16 entry), the microchannel of the substrate 18 may be exposed to atmospheric pressure through opening 26, which is in close proximity to valve/pressure sensor 28. As a result of atmospheric pressure exposure, the fluid 16 will traverse the microchannel due to capillary pressure. The fluid viscosity can be quantified by precisely measuring the length of the fluid column inside the microchannel and its velocity. This method produces viscosity measurements in a range of shear rates defined by the fluid 16 and the dimensions of the microchannel.

By nestling the micro-channeled substrate 18 between a light source 12 (e.g., collimated light source 12) of a specific wave-length and a photodetector 20 (e.g., a reverse-biased photodiode 20), the instantaneous length of the fluid column can be measured by quantifying the amount of shadow it casts. That is, the less light 14 that passes through optical lens 24 to be received by photodetector 20, the less signal photodetector 20 produces. As such, as the fluid column 17 progresses through the microchannel and obstructs optical lens 24, the less light 14 the detector 20 receives (see FIG. 2). In certain embodiments, detector 20 includes a selectively transparent mask 22 positioned thereon.

FIG. 2 shows a schematic of the functionality of an exemplary assembly 10. In general, only unobstructed light 14 reaches the photodiode 20 because the light 14 cannot transmit through the fluid/liquid 16 in the microchannel of substrate 18. The photodiode electrical response is then proportional to the fluid/liquid 16 progression through the microchannel.

By storing this information, one can record the fluid column length at specific times and thus compute its velocities at those times by finding the change in column length with respect to time.

Viscosity Measurement:

The shear stress ($\tau_w$) applied on the fluid/liquid 16 can be expressed as:

$$\tau_w = \frac{\Delta P}{L(t)} \frac{d}{2}$$

Where $\Delta P$ is the pressure applied on the fluid/liquid, $L(t)$ is the length of the fluid/liquid column at time t, and d is the height of the microchannel. Using the shear stress, one can compute the shear rate ($\dot{\gamma}w$) and the viscosity ($\eta$) to be:

$$\dot{\gamma}_w = \frac{6v(t)}{d}\left(\frac{2}{3} + \frac{1}{3n}\right)$$

$$\eta = \frac{\tau_w}{\dot{\gamma}_w}$$

Where v(t) is the velocity of the fluid column at a time t, and n is a constant defined by the fluid/liquid called the power law exponent, which can be found by curve fitting the equation $$L(t) = \frac{1}{Cv(t)^n},$$

where is a constant, to the gathered data (Srivastava and Burns 2006).

Pressure Measurement:

Capillary pressure can be measured by clamping the far microchannel exit. Provided that the microchannel material does not let air permeate through it, the air inside the microchannel will be compressed and an equilibrium will be reached between the capillary pressure of the fluid column and the compressed air.

Thus, $$\Delta P = P_{atm}\left(\frac{V_0}{V_1} - 1\right),$$

where $P_{atm}$ is the atmospheric pressure, $V_0$ is the original volume of the microchannel up to the clamp, and $V_1$ is the volume of compressed air in the microchannel (Srivastava and Burns 2006). Once the measurement has been taken, the clamp may be released, exposing the far end of the microchannel to atmospheric pressure.

Alternatively, the capillary pressure can be measured directly by means of a pressure sensor.

Capillary pressure can be replaced as the pressure applied on the sample liquid by applying a known negative pressure on the far end of the microchannel by a controlled pressure pump. Provided that the effects of capillary pressure are negligible relative to the negative pressure applied by the pressure pump, the magnitude of the applied negative pressure can be used in place of the negative capillary pressure measurement. A negligible capillary pressure can be achieved by enlarging the microchannel. In this case, a pressure sensor could corroborate that the desired negative pressure is achieved by a pressure pump.

Figure 5:
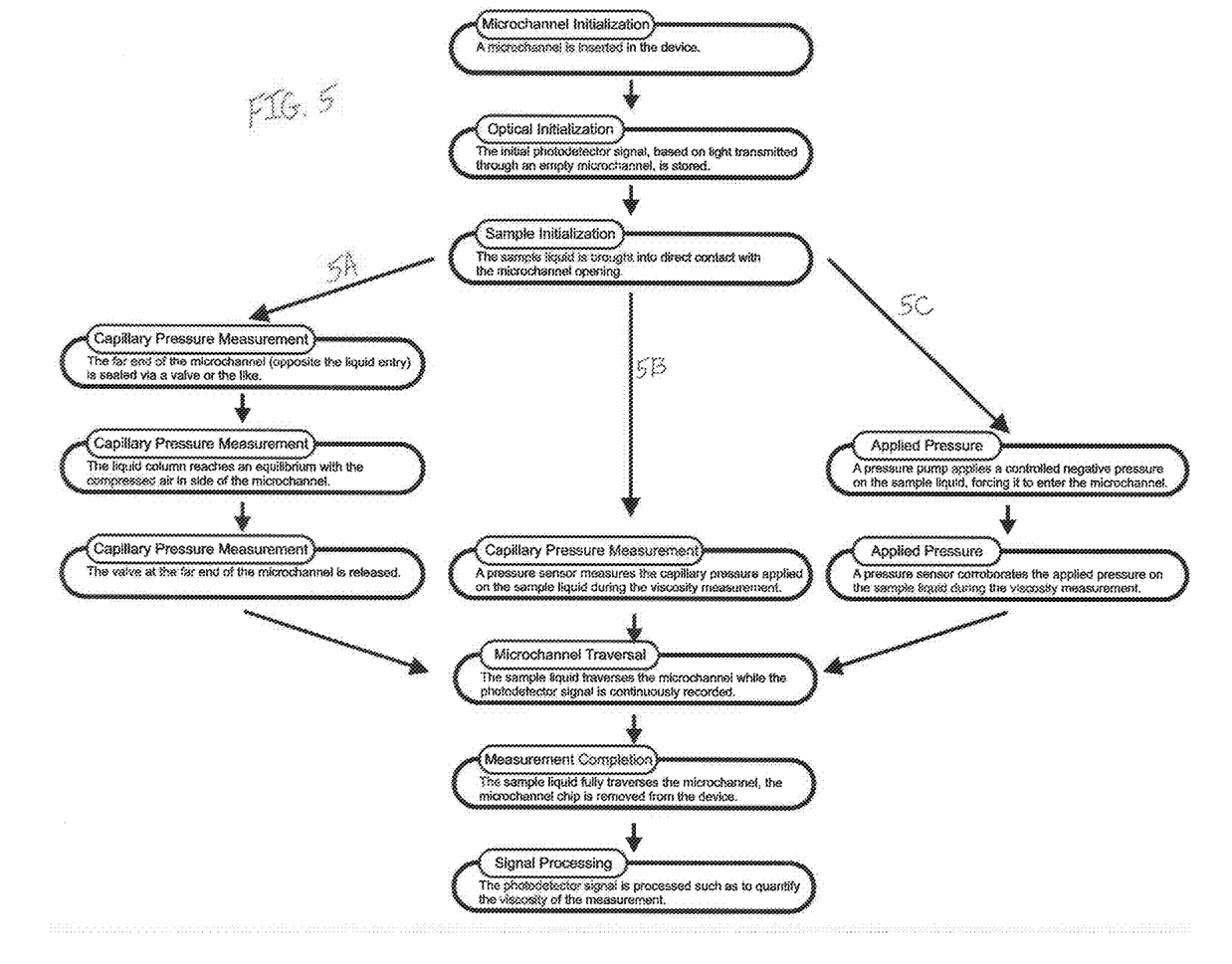

FIG. 5 is a flowchart depicting three modes of operation for an exemplary viscosity measuring assembly 10 according to the present disclosure. As shown in FIG. 5, a viscosity measuring assembly 10 can be constructed and/or operated in at least three different configurations—Arrow/flow 5A; Arrow/flow 5B; Arrow/flow 5C.

More particularly and in one embodiment (Arrow/flow 5A), a user may insert a micro-channeled substrate 18 into assembly 10 (Micro-channel Initialization). The initial photodetector signal, based on light transmitted through an empty microchannel can be stored (Optical Initialization). The sample liquid 16 can be brought into direct contact with the opening to the microchannel (Sample Initialization). The far end of the microchannel (opposite sample 16 entry) can be sealed via a valve or the like (Capillary Pressure Measurement). The liquid column reaches an equilibrium with the compressed air inside of the microchannel (Capillary Pressure Measurement). The valve at the far end of the microchannel can be released (Capillary Pressure Measurement). The sample liquid 16 traverses the microchannel while the photodetector signal is continuously recorded (Microchannel Traversal). The sample liquid fully traverses the microchannel, and the microchannel chip is removed from the assembly 10 (Measurement Completion). The photodetector signal is processed such as to quantify the viscosity of the measurement (Signal Processing).

In another embodiment and as shown as Arrow/flow 5B of FIG. 5, a user may insert a micro-channeled substrate 18 into assembly 10 (Micro-channel Initialization). The initial photodetector signal, based on light transmitted through an empty microchannel can be stored (Optical Initialization). The sample liquid 16 can be brought into direct contact with the opening to the microchannel (Sample Initialization). A pressure sensor can measure the capillary pressure applied on the sample 16 during the viscosity measurement (Capillary Pressure Measurement). The sample liquid 16 traverses the microchannel while the photodetector signal is continuously recorded (Microchannel Traversal). The sample liquid fully traverses the microchannel, and the microchannel chip is removed from the assembly 10 (Measurement Completion). The photodetector signal is processed such as to quantify the viscosity of the measurement (Signal Processing).

In another embodiment and as shown as Arrow/flow 5C of FIG. 5, a user may insert a micro-channeled substrate 18 into assembly 10 (Micro-channel Initialization). The initial photodetector signal, based on light transmitted through an empty microchannel can be stored (Optical Initialization). The sample liquid 16 can be brought into direct contact with the opening to the microchannel (Sample Initialization). A pressure pump can apply a controlled negative pressure on the sample 16, forcing it to enter the microchannel (Applied Pressure). The sample liquid 16 traverses the microchannel while the photodetector signal is continuously recorded (Microchannel Traversal). The sample liquid fully traverses the microchannel, and the microchannel chip is removed from the assembly 10 (Measurement Completion). The photodetector signal is processed such as to quantify the viscosity of the measurement (Signal Processing).

Figure 3:
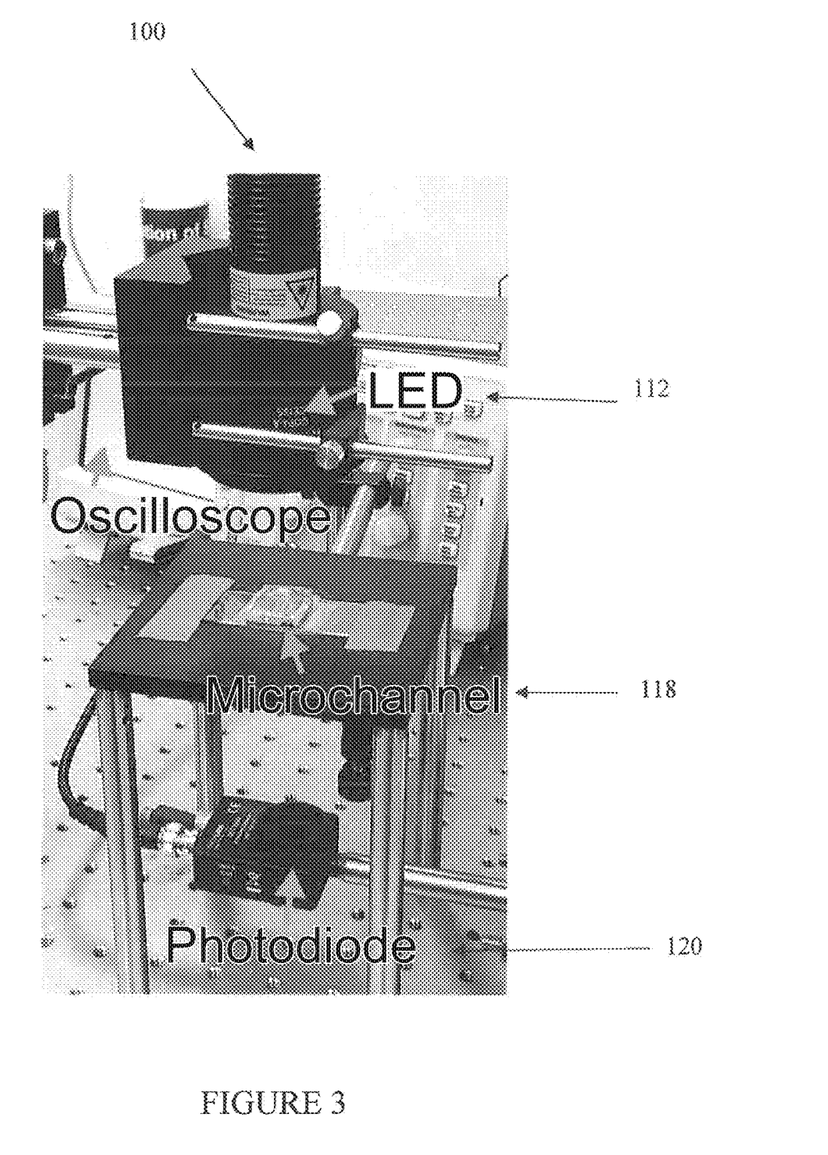
FIG. 3 is a side perspective view of another exemplary viscosity measuring assembly according to the present disclosure.

Validation:

As shown in FIG. 3, a laboratory assembly/system 100 has been developed and used to validate the working parameters of the proposed measuring assembly 100, and to measure the viscosity of a suspension of red blood cells in Alsever's solution. The laboratory assembly 100 set-up featured a number of more expensive tools that expedited the ability to take measurements (see FIG. 3).

As shown in FIG. 3, this assembly 100 utilized a collimated green LED light 112, because green light is the light that red blood cells most readily absorb in the visible spectrum. A lens was used that focused the light that passed through the micro-channeled substrate 118 to a small reverse-biased photodiode 120. The photodiode signal was recorded with an oscilloscope.

In order to measure the capillary pressure, the far end of the microchannel was connected to a pressure pump, and the applied pressure was adjusted until the fluid/liquid column stopped progressing through the microchannel.

Figure 4A:
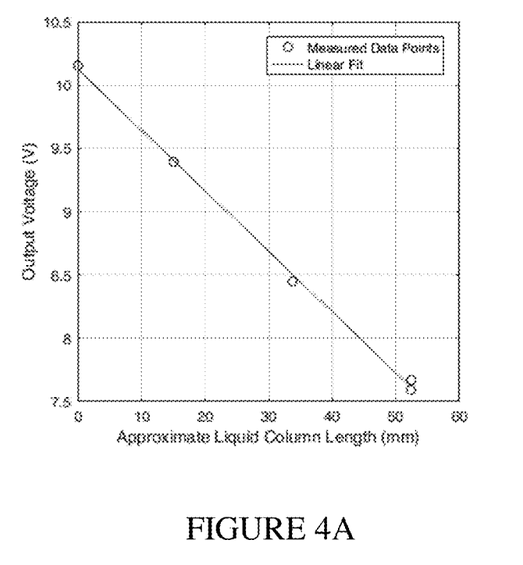

With this method a capillary pressure of approximately 15 mbar was measured, and it was confirmed that this pressure was uniform throughout the microchannel of substrate 118. Furthermore, it was also confirmed that the signal produced by the photodiode 120 in response to the length of fluid/liquid column was both linear and repeatable (see FIG. 4A). Because the signal was linear ($p<0.05$), it was not necessary to independently calibrate each assembly. It was sufficient to record the signal output before any fluid/liquid enters the microchannel and the signal output after the fluid/liquid fully traverses the microchannel.

Figure 4B:
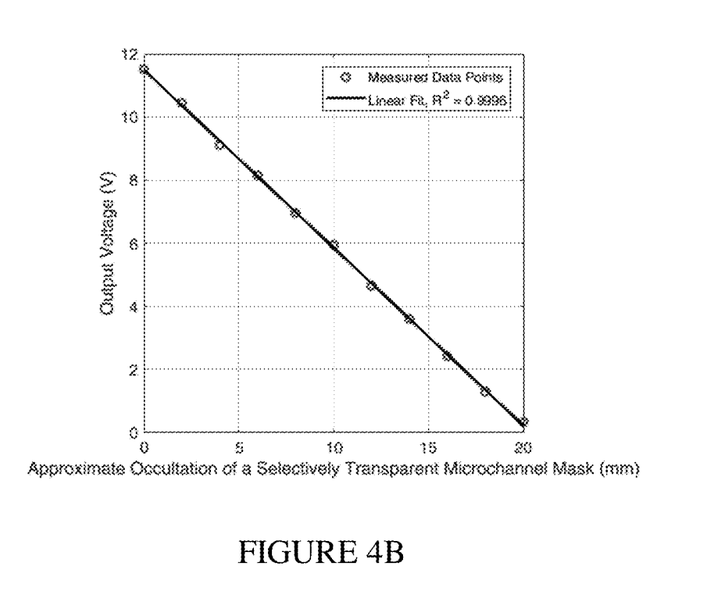
FIG. 4B shows that the photodiode signal corresponding to the manual occultation of a selectively transparent microchannel mask is linear (p<0.01); minor variations occurred at each point due to the manual estimation of the occultation distance and because the LED light source was not perfectly collimated.
Figure 4C:
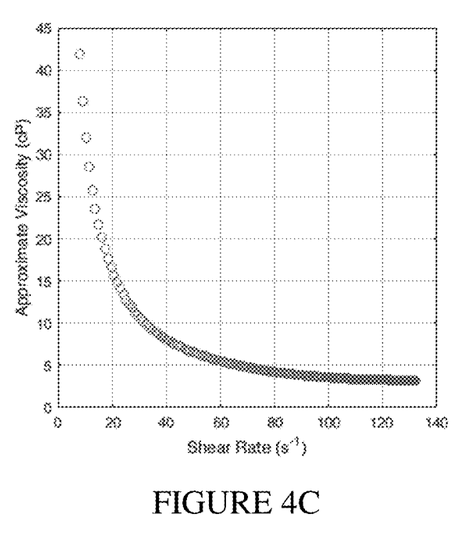

As shown in FIG. 4B, it was also confirmed that the photodiode signal corresponding to the manual occultation of a selectively transparent microchannel mask is linear ($p<0.01$). Finally, the viscosity of a red blood cells suspension in Alsever's solution was measured at an approximate hematocrit of 40% (see FIG. 4C).

Although the systems/methods of the present disclosure have been described with reference to exemplary embodiments thereof, the present disclosure is not limited to such exemplary embodiments/implementations. Rather, the systems/methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

The invention claimed is:

1. A measuring assembly comprising:
a substrate having a microchannel extending from a first end to a second end and defining a microchannel path therebetween;
a single light source positioned over a top surface of the substrate;
an optical lens and a single sensor positioned under a bottom surface of the substrate, the optical lens being configured and positioned so as to direct light from the single light source to the single sensor;
wherein the single sensor is adapted to detect light directed to it by the optical lens from the single light source over the full extent of the microchannel path and, based on shadows cast by a fluid sample as it traverses the microchannel path, (i) measure an instantaneous length of the fluid sample by quantifying the amount of shadow cast, and (ii) produce proportional signals that are utilized to measure progression of the fluid sample through the microchannel path to determine the viscosity of the fluid sample.

2. The assembly of claim 1, wherein the fluid sample is an opaque or transparent liquid.

3. The assembly of claim 1, wherein the fluid sample is blood.

4. The assembly of claim 1, wherein the light source is a collimated low coherence light source.

5. The assembly of claim 1, wherein the substrate is transparent.

6. The assembly of claim 1, wherein the sensor is a photodetector.

7. The assembly of claim 1, wherein the sensor is a reverse-biased photodiode.

8. The assembly of claim 1, wherein the light source and the sensor are not directly exposed to the fluid sample during introduction of the fluid sample to the first end of the microchannel.

9. The assembly of claim 1, wherein the fluid sample is about 500 µL or less.

10. The assembly of claim 1 further comprising a pressure sensor configured and adapted to measure the pressure inside the microchannel.

11. The assembly of claim 1 further comprising a heating element mounted with respect to the substrate, wherein the heating element is configured and adapted to control the temperature of the fluid sample during the viscosity measurement.

12. A measuring method comprising:
providing a substrate having a microchannel extending from a first end to a second end and defining a microchannel path therebetween;
positioning a single light source over a top surface of the substrate;
positioning an optical lens and a single sensor under a bottom surface of the substrate, the optical lens being configured and positioned so as to direct light from the single light source to the single sensor;
introducing a fluid sample to the first end of the microchannel; and
detecting light directed to the single sensor by the optical lens from the single light source over the full extent of the microchannel path and, based on shadows cast by a fluid sample as it traverses the microchannel path, to measure an instantaneous length of the fluid sample by quantifying the amount of shadow cast, and produce proportional signals that are utilized to measure how far along the microchannel path the fluid sample has progressed to determine the viscosity of the fluid sample.

13. The method of claim 12, wherein the fluid sample is an opaque or transparent liquid.

14. The method of claim 12, wherein the fluid sample is blood.

15. The method of claim 12, wherein the light source is a collimated low coherence light source.

16. The method of claim 12, wherein the substrate is transparent.

17. The method of claim 12, wherein the sensor is a photodetector.

18. The method of claim 12, wherein the sensor is a reverse-biased photodiode.

19. The method of claim 12, wherein the light source and the sensor are not directly exposed to the fluid sample during introduction of the fluid sample to the first end of the microchannel.

20. The method of claim 12, wherein the fluid sample is about 500 µL or less.

21. The method of claim 12, further comprising a pressure sensor configured and adapted to measure the pressure inside the microchannel.

22. The method of claim 12, further comprising a heating element mounted with respect to the substrate, wherein the heating element is configured and adapted to control the temperature of the fluid sample during the viscosity measurement.

* * * * *